United States Patent
Kaula et al.

(10) Patent No.: US 8,983,616 B2
(45) Date of Patent: Mar. 17, 2015

(54) METHOD AND SYSTEM FOR ASSOCIATING PATIENT RECORDS WITH PULSE GENERATORS

(75) Inventors: Norbert Kaula, Arvada, CO (US); Yohannes Iyassu, Denver, CO (US); Scott Drees, Dallas, TX (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/604,197

(22) Filed: Sep. 5, 2012

(65) Prior Publication Data
US 2014/0067014 A1    Mar. 6, 2014

(51) Int. Cl.
A61N 1/08    (2006.01)
A61N 1/372    (2006.01)
A61B 5/00    (2006.01)

(52) U.S. Cl.
CPC ............ *A61N 1/37247* (2013.01); *A61B 5/744* (2013.01)
USPC .................... 607/59; 607/30; 607/32; 607/60

(58) Field of Classification Search
CPC ........... A61N 1/37247; A61N 1/37252; A61N 1/37264; A61B 5/744; A61B 5/7435
USPC .......................................... 607/30–32, 59, 60
See application file for complete search history.

(56) References Cited

U.S. PATENT DOCUMENTS

| | | | |
|---|---|---|---|
| 4,432,360 A | 2/1984 | Mumford et al. | |
| 5,286,202 A | 2/1994 | De Gyarfas et al. | |
| 5,304,206 A | 4/1994 | Baker, Jr. et al. | |
| 5,312,446 A | 5/1994 | Holschbach et al. | |
| 5,370,672 A | 12/1994 | Fowler et al. | |
| 5,383,914 A | 1/1995 | O'Phelan | |
| 5,421,830 A | 6/1995 | Epstein et al. | |
| 5,628,776 A | 5/1997 | Paul et al. | |

(Continued)

FOREIGN PATENT DOCUMENTS

| | | |
|---|---|---|
| EP | 0761255 | 3/1997 |
| EP | 1192972 | 4/2002 |

(Continued)

OTHER PUBLICATIONS

Extended European Search Report issued for Patent Application No. 13182618.2, dated Dec. 13, 2013, 7 pgs.

(Continued)

*Primary Examiner* — Carl H Layno
*Assistant Examiner* — Eugene Wu
(74) *Attorney, Agent, or Firm* — Haynes and Boone, LLP

(57) ABSTRACT

The present disclosure involves a medical system. The medical system includes a medical device configured to deliver a medical therapy to a patient and store an electronic patient record that includes visual identification information of the patient. The medical system includes a clinician programmer configured to program the medical device. The clinician programmer includes a display screen. The clinician programmer includes a transceiver configured to conduct electronic communication with external devices. The clinician programmer includes a memory storage configured to store machine-readable code. The clinician programmer includes a computer processor configured to execute the machine-readable code to: establish an electronic communication with the medical device via the transceiver; and display the electronic patient record, including the visual identification information of the patient, on the display screen after the electronic communication has been established.

42 Claims, 10 Drawing Sheets

(56) References Cited

U.S. PATENT DOCUMENTS

| | | | |
|---|---|---|---|
| 5,713,937 | A | 2/1998 | Nappholz et al. |
| 5,722,999 | A * | 3/1998 | Snell .............................. 607/32 |
| 5,724,996 | A | 3/1998 | Piunti |
| 5,819,740 | A | 10/1998 | Muhlenberg |
| 5,842,976 | A * | 12/1998 | Williamson .................. 600/300 |
| 5,879,374 | A | 3/1999 | Powers et al. |
| 5,905,500 | A | 5/1999 | Kamen et al. |
| 5,938,690 | A | 8/1999 | Law et al. |
| 5,973,968 | A | 10/1999 | Schu et al. |
| 6,016,447 | A | 1/2000 | Juran et al. |
| 6,016,448 | A | 1/2000 | Busacker et al. |
| 6,052,624 | A | 4/2000 | Mann |
| 6,083,156 | A | 7/2000 | Lisiecki |
| 6,148,233 | A | 11/2000 | Owen et al. |
| 6,154,675 | A | 11/2000 | Juran et al. |
| 6,216,036 | B1 | 4/2001 | Jenkins et al. |
| 6,246,414 | B1 | 6/2001 | Kawasaki |
| 6,249,705 | B1 | 6/2001 | Snell |
| 6,278,890 | B1 | 8/2001 | Chassaing et al. |
| 6,307,554 | B1 | 10/2001 | Arai et al. |
| 6,308,102 | B1 | 10/2001 | Sieracki et al. |
| 6,345,200 | B1 | 2/2002 | Mouchawar et al. |
| 6,386,882 | B1 | 5/2002 | Linberg |
| 6,442,432 | B2 | 8/2002 | Lee |
| 6,525,727 | B1 | 2/2003 | Junkins et al. |
| 6,564,104 | B2 | 5/2003 | Nelson et al. |
| 6,587,104 | B1 | 7/2003 | Hoppe |
| 6,611,267 | B2 | 8/2003 | Migdal et al. |
| 6,622,048 | B1 | 9/2003 | Mann et al. |
| 6,669,631 | B2 | 12/2003 | Norris et al. |
| 6,786,405 | B2 | 9/2004 | Wiedenhoefer |
| 6,852,080 | B2 | 2/2005 | Bardy |
| 6,882,982 | B2 | 4/2005 | McMenimen et al. |
| 6,895,280 | B2 | 5/2005 | Meadows et al. |
| 6,920,360 | B2 | 7/2005 | Lee et al. |
| 6,931,155 | B1 | 8/2005 | Gioia |
| 6,961,448 | B2 | 11/2005 | Nichols et al. |
| 6,961,617 | B1 | 11/2005 | Snell |
| 7,003,349 | B1 | 2/2006 | Andersson et al. |
| 7,034,823 | B2 | 4/2006 | Dunnett |
| 7,058,453 | B2 | 6/2006 | Nelson et al. |
| 7,060,030 | B2 | 6/2006 | Von Arx et al. |
| 7,065,409 | B2 | 6/2006 | Mazar |
| 7,066,910 | B2 | 6/2006 | Bauhahn et al. |
| 7,076,303 | B2 | 7/2006 | Linberg |
| 7,087,015 | B1 | 8/2006 | Comrie et al. |
| 7,092,761 | B1 | 8/2006 | Cappa et al. |
| 7,107,102 | B2 | 9/2006 | Daignault et al. |
| 7,142,923 | B2 | 11/2006 | North et al. |
| 7,181,286 | B2 | 2/2007 | Sieracki et al. |
| 7,181,505 | B2 | 2/2007 | Haller et al. |
| 7,184,837 | B2 | 2/2007 | Goetz |
| 7,236,827 | B2 * | 6/2007 | Vitt et al. ........................ 607/27 |
| 7,239,926 | B2 | 7/2007 | Goetz |
| 7,240,833 | B2 * | 7/2007 | Zarembo ...................... 235/385 |
| 7,266,412 | B2 | 9/2007 | Stypulkowski |
| 7,299,085 | B2 | 11/2007 | Bergelson et al. |
| 7,359,751 | B1 | 4/2008 | Erickson et al. |
| 7,373,204 | B2 | 5/2008 | Gelfand et al. |
| 7,440,806 | B1 | 10/2008 | Whitehurst et al. |
| 7,452,336 | B2 | 11/2008 | Thompson |
| 7,463,927 | B1 | 12/2008 | Chaouat |
| 7,474,223 | B2 | 1/2009 | Nycz et al. |
| 7,481,759 | B2 | 1/2009 | Whitehurst et al. |
| 7,489,970 | B2 | 2/2009 | Lee et al. |
| 7,496,403 | B2 | 2/2009 | Cao et al. |
| 7,499,048 | B2 | 3/2009 | Sieracki et al. |
| 7,505,815 | B2 | 3/2009 | Lee et al. |
| 7,551,960 | B2 | 6/2009 | Forsberg et al. |
| 7,602,384 | B2 | 10/2009 | Rosenberg et al. |
| 7,617,002 | B2 | 11/2009 | Goetz |
| 7,627,372 | B2 | 12/2009 | Vaisnys et al. |
| 7,640,059 | B2 | 12/2009 | Forsberg et al. |
| 7,650,888 | B2 * | 1/2010 | Maschke ....................... 128/899 |
| 7,657,317 | B2 | 2/2010 | Thacker et al. |
| 7,685,005 | B2 | 3/2010 | Riff et al. |
| 7,711,603 | B2 | 5/2010 | Vanker et al. |
| 7,720,549 | B2 | 5/2010 | Schroeppel et al. |
| 7,747,330 | B2 | 6/2010 | Nolan et al. |
| 7,774,067 | B2 | 8/2010 | Keacher et al. |
| 7,778,710 | B2 | 8/2010 | Propato |
| 7,801,596 | B2 | 9/2010 | Fischell et al. |
| 7,801,611 | B2 | 9/2010 | Persen et al. |
| 7,805,199 | B2 | 9/2010 | KenKnight et al. |
| 7,822,483 | B2 | 10/2010 | Stone et al. |
| 7,853,323 | B2 | 12/2010 | Goetz |
| 7,885,712 | B2 | 2/2011 | Goetz et al. |
| 7,890,180 | B2 | 2/2011 | Quiles et al. |
| 7,928,995 | B2 | 4/2011 | Daignault |
| 7,934,508 | B2 | 5/2011 | Behm |
| 7,940,933 | B2 | 5/2011 | Corndorf |
| 7,953,492 | B2 | 5/2011 | Corndorf |
| 7,953,612 | B1 | 5/2011 | Palmese et al. |
| 7,957,808 | B2 | 6/2011 | Dawant et al. |
| 7,978,062 | B2 | 7/2011 | LaLonde et al. |
| 7,991,482 | B2 | 8/2011 | Bradley |
| 8,014,863 | B2 | 9/2011 | Zhang et al. |
| 8,021,298 | B2 | 9/2011 | Baird et al. |
| 8,027,726 | B2 | 9/2011 | Ternes |
| 8,046,241 | B1 | 10/2011 | Dodson |
| 8,060,216 | B2 | 11/2011 | Greenberg et al. |
| 8,068,915 | B2 | 11/2011 | Lee et al. |
| 8,068,918 | B2 | 11/2011 | Vallapureddy et al. |
| 8,078,440 | B2 | 12/2011 | Otto et al. |
| 8,082,162 | B2 | 12/2011 | Flood |
| 8,121,702 | B2 | 2/2012 | King |
| 8,135,566 | B2 | 3/2012 | Marshall et al. |
| 8,140,160 | B2 | 3/2012 | Pless et al. |
| 8,140,167 | B2 | 3/2012 | Donders et al. |
| 8,160,328 | B2 | 4/2012 | Goetz et al. |
| 8,160,704 | B2 | 4/2012 | Freeberg |
| 8,165,385 | B2 | 4/2012 | Reeves et al. |
| 8,187,015 | B2 | 5/2012 | Boyd et al. |
| 8,200,324 | B2 | 6/2012 | Shen et al. |
| 8,200,340 | B2 | 6/2012 | Skelton et al. |
| 8,219,206 | B2 | 7/2012 | Skelton et al. |
| 8,233,991 | B2 | 7/2012 | Woods et al. |
| 8,246,680 | B2 | 8/2012 | Betz et al. |
| 8,249,713 | B2 | 8/2012 | Fang et al. |
| 8,255,060 | B2 | 8/2012 | Goetz et al. |
| 8,323,218 | B2 | 12/2012 | Davis et al. |
| 8,326,433 | B2 | 12/2012 | Blum et al. |
| 8,340,775 | B1 | 12/2012 | Cullen et al. |
| 8,382,666 | B1 | 2/2013 | Mao et al. |
| 8,386,032 | B2 | 2/2013 | Bachinski et al. |
| 8,401,666 | B2 | 3/2013 | Skelton et al. |
| 8,428,727 | B2 | 4/2013 | Bolea et al. |
| 2001/0037220 | A1 | 11/2001 | Merry et al. |
| 2003/0009203 | A1 * | 1/2003 | Lebel et al. ...................... 607/60 |
| 2003/0045903 | A1 * | 3/2003 | Vitt et al. .......................... 607/2 |
| 2003/0076301 | A1 | 4/2003 | Tsuk et al. |
| 2003/0107572 | A1 | 6/2003 | Smith et al. |
| 2003/0139652 | A1 | 7/2003 | Kang et al. |
| 2003/0171911 | A1 | 9/2003 | Fairweather |
| 2003/0177031 | A1 | 9/2003 | Malek |
| 2004/0088374 | A1 | 5/2004 | Webb et al. |
| 2004/0122477 | A1 | 6/2004 | Whitehurst et al. |
| 2004/0210273 | A1 * | 10/2004 | Wang ............................... 607/59 |
| 2005/0107831 | A1 | 5/2005 | Hill et al. |
| 2005/0149356 | A1 | 7/2005 | Cyr et al. |
| 2005/0168460 | A1 | 8/2005 | Razdan et al. |
| 2005/0277872 | A1 | 12/2005 | Colby et al. |
| 2006/0020304 | A1 | 1/2006 | Torgerson et al. |
| 2006/0089888 | A1 | 4/2006 | Roger |
| 2006/0100832 | A1 | 5/2006 | Bowman |
| 2006/0100907 | A1 | 5/2006 | Holland et al. |
| 2006/0212096 | A1 * | 9/2006 | Stevenson ....................... 607/60 |
| 2006/0241720 | A1 | 10/2006 | Woods et al. |
| 2006/0242159 | A1 | 10/2006 | Bishop et al. |
| 2006/0282168 | A1 | 12/2006 | Sherman et al. |
| 2007/0078497 | A1 | 4/2007 | Vandanacker |
| 2007/0093998 | A1 | 4/2007 | El-Baroudi et al. |
| 2007/0179349 | A1 | 8/2007 | Hoyme et al. |
| 2007/0203537 | A1 | 8/2007 | Goetz et al. |

(56) References Cited

U.S. PATENT DOCUMENTS

| | | |
|---|---|---|
| 2007/0203538 A1 | 8/2007 | Stone et al. |
| 2007/0203543 A1 | 8/2007 | Stone et al. |
| 2007/0203547 A1* | 8/2007 | Costello et al. ............... 607/59 |
| 2007/0213790 A1 | 9/2007 | Nolan et al. |
| 2007/0260292 A1* | 11/2007 | Faltys et al. ................. 607/57 |
| 2008/0004675 A1 | 1/2008 | King et al. |
| 2008/0033303 A1 | 2/2008 | Wariar et al. |
| 2008/0046036 A1 | 2/2008 | King et al. |
| 2008/0058900 A1* | 3/2008 | Berthelsdorf et al. .......... 607/59 |
| 2008/0140160 A1* | 6/2008 | Goetz et al. .................. 607/60 |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1* | 1/2009 | Hennig ......................... 607/30 |
| 2009/0048871 A1 | 2/2009 | Skomra |
| 2009/0062887 A1* | 3/2009 | Mass et al. ................... 607/60 |
| 2009/0089034 A1 | 4/2009 | Penney et al. |
| 2009/0099624 A1 | 4/2009 | Kokones et al. |
| 2009/0132009 A1 | 5/2009 | Torgerson et al. |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennet et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0112601 A1* | 5/2011 | Meadows et al. ............... 607/42 |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0196449 A1* | 8/2011 | Jenison ......................... 607/60 |
| 2011/0196455 A1 | 8/2011 | Sieracki et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0109258 A1* | 5/2012 | Cinbis et al. .................. 607/60 |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Connor et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| EP | 2277586 | 1/2011 |
| WO | WO 9959106 | 11/1999 |
| WO | WO 02009808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Synalink Features, SynaMed Web Page, http://synamed.com/synalinkFeatures.html., Copyright 2010, 2 pgs.
Boston Scientific Corporation, "Boston Scientific Precision Spectra System Programming Manual", Copyright 2010, 580 pgs.

* cited by examiner

| ▼PATIENT NAME | ▲PATIENT NUMBER | ▲DATE OF BIRTH | ▲xPG ID |
|---|---|---|---|
| Public, John Q. | 0000002 | 08\|22\|1976 | 0x000002 |
| Jackson, Bo | 0000007 | 01\|25\|1970 | 0x000001 |
| Washington, George | 0000004 | 02\|17\|1957 | 0x000003 |
| Ruth, Babe | 0000005 | 09\|24\|1981 | 0x000004 |
| Sterling, Archer | 0000006 | 11\|06\|1938 | 0x000005 |
| Smith, John | 0000008 | 09\|30\|1964 | 0x000006 |

Fig. 3

METHOD AND SYSTEM FOR ASSOCIATING PATIENT RECORDS WITH PULSE GENERATORS

BACKGROUND

As medical device technologies continue to evolve, active implantable medical devices have gained increasing popularity in the medical field. For example, one type of implantable medical device includes neurostimulator devices, which are battery-powered or battery-less devices that are designed to deliver electrical stimulation to a patient. Through proper electrical stimulation, the neurostimulator devices can provide pain relief for patients.

An implantable medical device (for example a neurostimulator) can be controlled using an electronic programming device such as a clinician programmer or a patient programmer. These programmers can be used by medical personnel or the patient to define the particular electrical stimulation therapy to be delivered to a target area of the patient's body, or alter one or more stimulation parameters of the electrical stimulation therapy. Advances in the medical device field have improved these electronic programmers. However, the capabilities of these electronic programmers have not been fully utilized. For example, the electronic programmers have not been fully utilized to ensure that the electrical stimulation therapy programming is done to a correct patient with the correct medical device.

Therefore, although electronic programming devices for controlling medical devices have been generally adequate for their intended purposes, they have not been entirely satisfactory in every aspect.

SUMMARY

One aspect of the present disclosure involves a medical system. The medical system includes: a medical device configured to deliver a medical therapy to a patient and store an electronic patient record that includes visual identification information of the patient; and a clinician programmer configured to program the medical device, wherein the clinician programmer includes: a display screen; a transceiver configured to conduct electronic communication with external devices; a memory storage configured to store machine-readable code; and a computer processor configured to execute the machine-readable code to: establish an electronic communication with the medical device via the transceiver; and display the electronic patient record, including the visual identification information of the patient, on the display screen after the electronic communication has been established.

Another aspect of the present disclosure involves a portable electronic programmer for programming one or more medical devices to deliver a medical therapy to a patient. The portable electronic programmer includes: a communications module configured to conduct electronic communication with external devices; a touch screen module configured to receive an input from a user and display an output to the user; a memory storage module configured to store machine-readable instructions; and a computer processor module configured to execute machine-readable instructions to perform the following tasks: discovering, at least in part via the communications module, a plurality of nearby medical devices; extracting a plurality of patient records from at least a subset of the nearby medical devices, wherein each patient record is stored electronically in a respective one of the nearby medical devices in the subset, and wherein each patient record contains visual identification information for a respective patient and a unique identifier for the medical device on which the patient record is stored; and displaying an arrangement of the patient records on the touch screen module, including displaying the visual identification information for the patient and the unique identifier for the medical device for each patient record.

Yet another aspect of the present disclosure involves a method of associating patient information with medical devices. The method includes: broadcasting a discovery message over a wireless network, the discovery message requesting nearby medical devices to each return a query response; receiving the query responses from the nearby medical devices, wherein each query response includes an electronic identifier for the respective medical device; showing the electronic identifiers on a display screen along with visual identification information of a plurality of patients, wherein each electronic identifier is paired with the visual identification information of a respective patient; and detecting, in response to a user interaction with the electronic identifiers of the medical devices or the visual identification information of the patients, a selected medical device for programming.

One more aspect of the present disclosure involves a programmable pulse generator for delivering a stimulation therapy to a patient. The programmable pulse generator includes: a transceiver component configured to conduct telecommunications with an external electronic programmer to receive one or more stimulation programs; a memory storage divided partitioned into a plurality of partitions, wherein a first one of the partitions is configured to store the stimulation programs, and wherein a second one of the partitions is configured to store personal information of the patient including visual identification information of the patient; and microcontroller and stimulation circuitry configured to generate electrical pulses of the stimulation therapy based on the stimulation programs.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIGS. 3-4 are example user interfaces displayed on an electronic programmer according to various aspects of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Electronic programmers have been used to configure or program active implantable medical devices such as neurostimulators so that they can be operated in a certain manner. These electronic programmers include clinician programmers and patient programmers, each of which may be a handheld device. A clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. However, the capabilities of existing programmers have not been fully utilized. For example, the existing programmers have not been utilized to make sure that the stimulation programming is done to the correct patient with the correct stimulation device. In more detail, a healthcare professional may use a programmer to find nearby stimulation devices for programming. However, since the healthcare professional may not be familiar with the target patient and may not be certain of which stimulation device is associated with the patient. Therefore, the healthcare professional may make a mistake and program the wrong stimulation device, or apply incorrect stimulation programs for the right stimulation device.

According to various aspects of the present disclosure, a system and method is implemented in which an electronic programmer such as a clinician programmer is used to help the user visually associate the target patient with a target stimulation device, thereby preventing or reducing the likelihood of programming errors.

Figure 1:
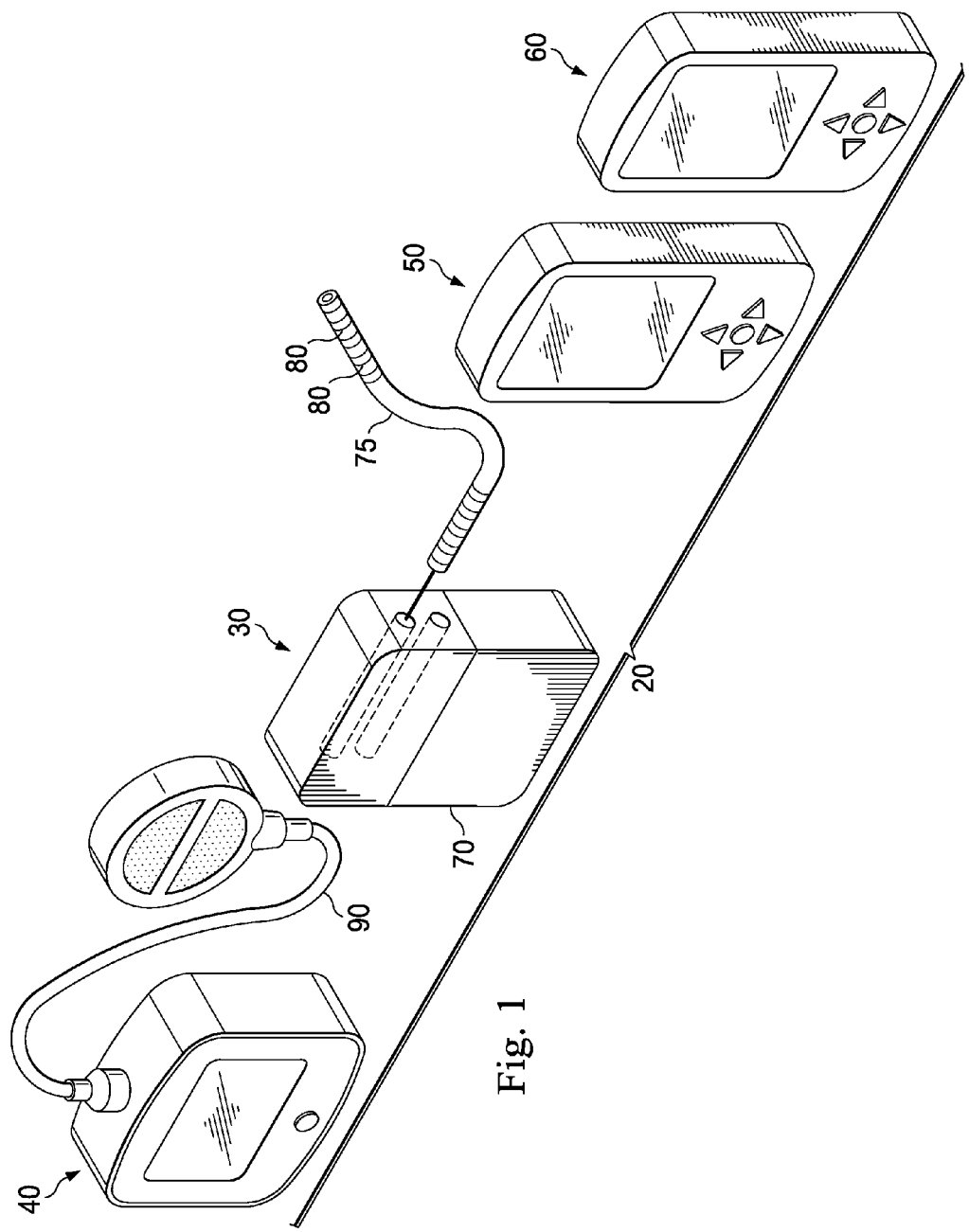
FIG. 1 is a simplified block diagram of a medical system according to various aspects of the present disclosure.

Referring to FIG. 1, a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

Figure 2:
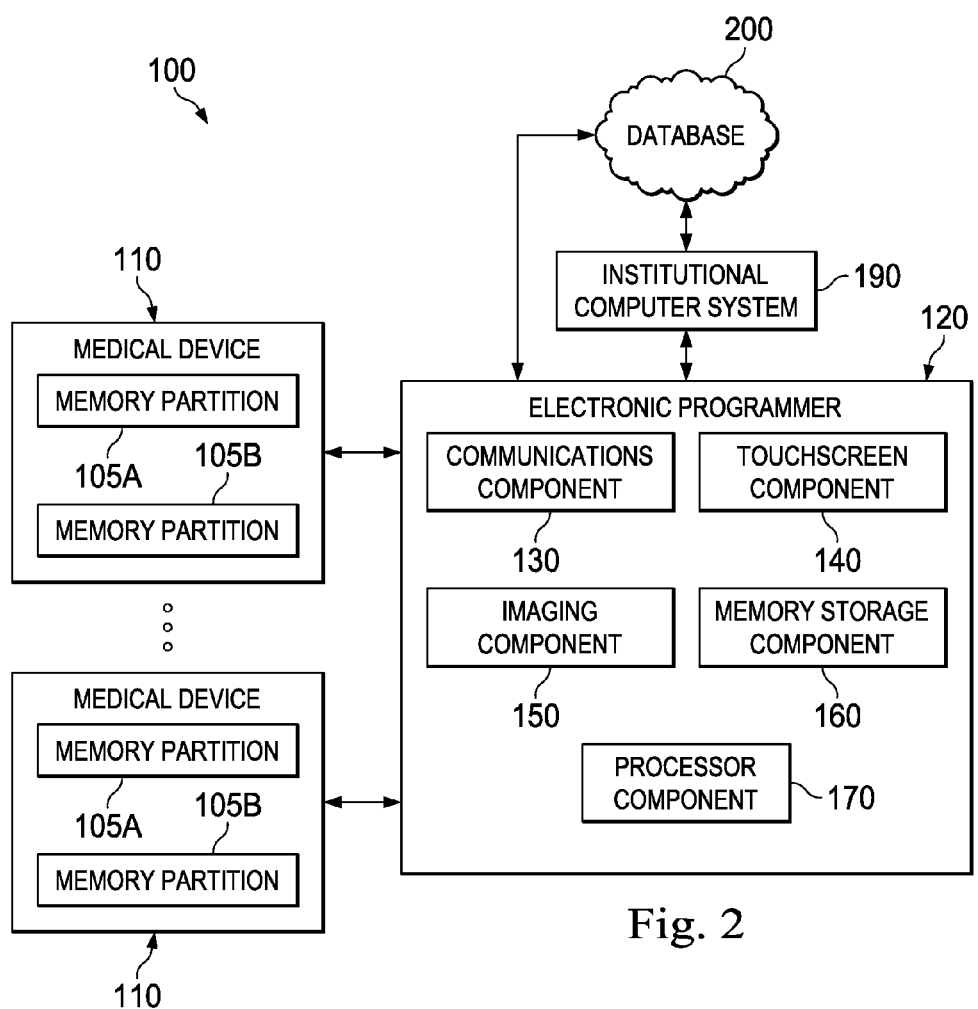
FIG. 2 is a simplified block diagram of a medical infrastructure according to various aspects of the present disclosure.

Referring now to FIG. 2, a simplified block diagram of a medical infrastructure 100 (which may also be considered a medical system) is illustrated according to various aspects of the present disclosure. The medical infrastructure 100 includes a plurality of medical devices 110. These medical devices 110 may each be a programmable medical device (or parts thereof) that can deliver a medical therapy to a patient. In some embodiments, the medical devices 110 may include a device of the neurostimulator system discussed above with reference to FIG. 1. For example, the medical devices 110 may be a pulse generator, an implantable lead, a charger, or portions thereof. It is understood that each of the medical devices 110 may be a different type of medical device. In other words, the medical devices 110 need not be the same type of medical device.

The medical devices 110 may each contain a partition-able memory storage 105. In other words, the memory for each medical device 110 may be divided or separated into a plurality of different mutually exclusive partitions. As an example, the memory storage 105 is partitioned into different and mutually exclusive partitions 105A and 105B herein, though it is understood that many more different partitions may be implemented. According to some embodiments, the data stored in the partition 105A is inaccessible by entities (for example, by an external clinician programmer) that also stores data in the partition 105B, and vice versa. Different types of data may be stored in these different partitions. For example, the memory partition 105A may be configured to store personal information of a patient for whom the medical device 110 is treating. The personal information may include visual identification information of the patient. Such visual identification information may include an electronic photograph or picture of the patient, or an electronic video of the patient. The personal information of the patient may also include other types of biometric, demographic, or biographical data of the patient, such as the name, residential address, email address, employment, phone number, birthdate, age, height, weight, blood type, medication taken, symptoms, and hospital identification number of the patient, etc.

The personal information may be a part of a patient's electronic record. In some embodiments, the patient's electronic record may also include an electronic unique identifier (for example the product number and/or serial number) of the medical device 110 associated with the patient. In some embodiments, the memory partition 105A becomes read-only after the patient's personal information has been written into it. In other words, the patient's personal information can only be retrieved (i.e., read), but not erased or otherwise overwritten. In other embodiments, the memory partition 105A may still be written after the patient's personal information has been written therein, but it can be updated only with that patient's information, and not another patient's information. To update the information in the memory partition 105A, a password may be needed in certain embodiments. In other words, the memory partition 105A may be password-protected.

In comparison, the memory partition 105B may be configured to store stimulation programs that are used to configure the various parameters (such as stimulation amplitude, pulse width, frequency, electrode configuration, etc.) of the electrical stimulation therapy to be delivered to the patient. These stimulation programs may be downloaded from external programmers (discussed below) and are modifiable or erasable. In some embodiments, the memory partition 105B is configured to block data associated with the personal information of the patient from being written therein, and the memory partition 105A is configured to block data associated with the stimulation programs from being written therein, thereby ensuring the mutual exclusivity between the memory partitions 105A and 105B.

The separation of the patient's personal information from the treatment or stimulation programs may improve the security and reliability of the medical device 110. Since the memory partitions 105A and 105B are separate and mutually exclusive from one another, it prevents data-overwriting errors from one partition to another. For instance, while the stimulation programs are downloaded into the memory partition 105B, no data from the stimulation programs will accidentally "spill over" into the memory partition 105A (reserved for the patient's personal information). Likewise, when the patient's personal information (which may include a video of the patient, which can be a large data file) is written into the memory partition 105A, no part of the data corresponding to the patient's personal information will spill over to the memory partition 105B. In this manner, neither memory partition is contaminated with undesired data, which may otherwise interfere with the intended operation of the memory partition.

The separation of the patient's personal information from the treatment or stimulation programs may also discourage or reduce unlawful "reprocessing" of the medical devices 110.

In more detail, a manufacturer may initially sell the medical device 110 (which is intended to be a "single use" product) to a patient (or to a hospital or clinician first). As a part of the transaction, the manufacturer typically agrees to a certain warranty of the "single use" medical device 110 to the purchaser as well as certain product liabilities resulting from the implantation or use of the medical device 110.

However, since the medical devices 110 may be expensive, some unrelated parties may wish to unlawfully re-use or "reprocess" these single use medical devices. As an example, theoretically, an implanted medical device 110 may be surgically removed from its original host patient (for instance after the original patient's death), and if it is still operational, it may then be sold to a third party at a lower price. These "reprocessing" transactions are often not carried out by reputable businesses and may compromise device quality, thereby exposing patients to risky devices and also imposing undue risks to the manufacturer in terms of warranty and product liability.

By making the medical device 110 partition-able, and by storing different types of data on different memory partitions, the present disclosure significantly reduces the "reprocessing" risks for patients and the manufacturers. Since the personal data stored in the memory partition 105A cannot be easily erased or overwritten by data from a second patient, it may be highly difficult and/or cumbersome to store the personal information for such second patient on the medical device 110, thereby discouraging unlawful "reprocessing" of the medical device. And even if the medical device has somehow been "reprocessed", the original patient's personal information stored on the medical device 110 may serve as evidence that the medical device has been previously implanted and has now been unlawfully "reprocessed."

The medical infrastructure 100 also includes an electronic programmer 120. In some embodiments, the electronic programmer 120 may be a clinician programmer, for example the clinician programmer 60 of FIG. 1 (or a similar programmer). In other embodiments, the electronic programmer 120 may be a patient programmer, for example the patient programmer 50 of FIG. 1 (or a similar programmer). In further embodiments, it is understood that the electronic programmer may be a tablet computer. In any case, the electronic programmer 120 is configured to program the stimulation parameters of the medical devices 110 so that a desired medical therapy can be delivered to a patient.

The electronic programmer 120 contains a communications component 130 that is configured to conduct electronic communications with external devices. For example, the communications device 130 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (WiFi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 120 contains a touchscreen component 140. The touchscreen component 140 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 120 may optionally include additional user input/output components that work in conjunction with the touchscreen component 140 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 120 contains an imaging component 150. The imaging component 150 is configured to capture an image of a target device via a scan. For example, the imaging component 150 may be a camera in some embodiments. The camera may be integrated into the electronic programmer 120. The camera can be used to take a picture of a medical device, or scan a visual code of the medical device, for example its barcode or Quick Response (QR) code.

The electronic programmer contains a memory storage component 160. The memory storage component 160 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 160 (or a portion thereof) may be configured as a local database capable of storing electronic records of medical devices and/or their associated patients. For example, in some embodiments, patient records that correspond to the patient records stored in the medical devices 110 may be stored in the memory storage component 160. In other words, the patient record stored at the medical devices 110 and the patient record stored on the clinician programmer 120 may be substantially copies of one another, and they can be synched, or one can be updated based on the other. It is understood that these patient records may also include the medical device identifier in some embodiments.

The electronic programmer contains a processor component 170. The processor component 170 may include a central processing unit (CPU), a graphics processing unit (GPU) a micro-controller, a digital signal processor (DSP), or another suitable electronic processor capable of handling and executing instructions. In various embodiments, the processor component 170 may be implemented using various digital circuit blocks (including logic gates such as AND, OR, NAND, NOR, XOR gates, etc.) along with certain software code. In some embodiments, the processor component 170 may execute one or more sequences computer instructions contained in the memory storage component 160 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 120 is not necessarily limited to the components 130-170 discussed above, but it may further include additional components that are used to carry out the programming tasks. These additional components are not discussed herein for reasons of simplicity. It is also understood that the medical infrastructure 100 may include a plurality of electronic programmers similar to the electronic programmer 120 discussed herein, but they are not illustrated in FIG. 2 for reasons of simplicity.

The medical infrastructure 100 also includes an institutional computer system 190. The institutional computer system 190 is coupled to the electronic programmer 120. In some embodiments, the institutional computer system 190 is a computer system of a healthcare institution, for example a hospital. The institutional computer system 190 may include one or more computer servers and/or client terminals that may each include the necessary computer hardware and software for conducting electronic communications and performing programmed tasks. In various embodiments, the institutional computer system 190 may include communications devices (e.g., transceivers), user input/output devices, memory storage devices, and computer processor devices that may share similar properties with the various components 130-170 of the electronic programmer 120 discussed above. For example, the institutional computer system 190 may include computer servers that are capable of electronically communicating with the electronic programmer 120 through the MICS protocol or another suitable networking protocol.

The medical infrastructure 100 includes a database 200. In various embodiments, the database 200 is a remote database—that is, located remotely to the institutional computer system 190 and/or the electronic programmer 120. The database 200 is electronically or communicatively (for example through the Internet) coupled to the institutional computer system 190 (or the electronic programmer) in a cloud-based architecture. The database 200 may also be communicatively coupled to the electronic programmer 120. The database 200 includes cloud-based resources, which may include one or more computers, such as mass storage computer servers, with adequate memory resources to handle requests from a variety of clients. The institutional computer system 190 and the electronic programmer 120 (or their respective users) may both be considered clients of the database 200. In certain embodiments, the functionality between the cloud-based resources and its clients may be divided up in any appropriate manner. For example, the electronic programmer 120 may perform basic input/output interactions with a user, but a majority of the processing and caching may be performed by the cloud-based resources in the database 200. However, other divisions of responsibility are also possible in various embodiments.

The database 200 may be a manufacturer's database in some embodiments. In other embodiments, the database 200 may be a database of a healthcare institution such as a hospital and may even be considered a part of the institutional computer system 190. Among other things, the database 200 may be configured to electronically store a plurality of patient records. For example, in some embodiments, patient records that correspond to the patient records stored in the medical devices 110 (or the ones stored on the clinician programmer 120) may be stored in the database 200. In other words, the patient record stored at the medical devices 110 (or on the clinician programmer 120) and the patient record stored on the database 200 may be substantially copies of one another, and they can be synched, or one can be updated based on the other. It is understood that these patient records may also include the medical device identifier in some embodiments.

The medical infrastructure 100 can be used to provide intuitive and reliable association between target patients and their medical devices, so that the right stimulation therapy can be delivered to the correct patient. This is explained in FIGS. 3-10 and the corresponding discussions below.

FIG. 3 illustrates a user interface 250A of an electronic programmer that illustrates a result of a medical device query. In more detail, as discussed above, the electronic programmer 120 has a touchscreen component 140 through which a touch-sensitive graphical user interface is displayed. The user interface 250A is a part of such touch-sensitive graphical user interface implemented on the touchscreen component 140.

The electronic programmer 120 (FIG. 2) such as a clinician programmer may be used by a healthcare professional to query for a list of medical devices 110 (FIG. 2), for example implantable or implanted pulse generators that are nearby. The electronic programmer 120 may request all (or some) of the queried medical devices 110 to return the respective patient records stored therein. As discussed above, the patient record may include personal information of each patient, including visual identification information such as electronic photographs or videos. The patient record may also include unique identifiers of the medical device 110 associated with the patient (i.e., the medical device in which the patient record is stored).

These patient records may be displayed in the user interface 250A as a part of the query result. Each patient record may include information such as the patient name, an image or video of the patient, patient number (for example a hospital identification number for the patient), date of birth, and the unique identifier of the medical device ("xPG ID"). The image or video of the patient may be acquired using the imaging component 150 of the electronic programmer 120 at a previous time, and the corresponding data file may be then stored in the medical device 110 (e.g., in the partition 105A). In some embodiments, the patient record (including the visual identification information) may also be stored in the electronic programmer 120 locally or remotely in the database 200 (FIG. 2). For patients whose visual identification information is missing (e.g., patient "Babe Ruth"), the healthcare professional may use information stored in the electronic programmer 120 or the remote database 200 to update the patient record stored in the medical device 110 associated with the patient.

It is understood that the patient records displayed in the user interface 250A may include additional (or less) patient information, for example the patient's biometric information such as his height, weight, gender, blood type, etc. The patient records may also include other relevant information of the patient, such as his address, employer, job title, symptoms, allergies, current medications, name of the treating physician, and stimulation programs being used to treat him, etc. In fact, what type of information is displayed in the user interface 250A may be customizable.

In some embodiments, the patient records are displayed in a sortable list form. In some embodiments, the list may be sortable based on the proximity of their respective medical device's proximity to the electronic programmer 120, or may be sortable based on an alphabetical order of the patient's names, or combinations thereof. Of course, the sorting of patient records may also be done using other criteria in alternative embodiments, for example by the age of the patient or the medical device identifier. In addition, although the patient records returned in the query result are displayed in the form of a list in the embodiment shown in FIG. 3, the records may also be displayed in other forms, such as a grid of icons, a virtual scrollable carousel, etc.

The healthcare professional may then click on any of the patient records to select a target medical device for programming. For example, the healthcare professional may select a patient record 260 (belonging to the patient named Bo Jackson) by clicking on it through the touchscreen. The patient record 260 becomes highlighted, and an interactive icon 270 may pop up to indicate the healthcare professional's selection of the patient record. In some embodiments, the icon 270 may indicate that the medical device is ready to be programmed. In other embodiments, the icon 270 may indicate that the patient record may be viewed in more detail, for example in the user interface 250B illustrated in FIG. 4.

Figure 4:

Referring to FIG. 4, a more detailed patient record 280 in FIG. 4 may contain additional information not shown in the list of patient records in FIG. 3. For example, these additional pieces of information may include the patient's birth date, name of treating physician, medical record number, symptoms, pain medications, implant date for the medical device, and home address and phone number. Of course, the patient record 280 is merely an example, and other patient records may include additional information or remove some of the information shown herein.

As discussed above, according to some embodiments, the patient records may be stored in any one of: the medical devices 110, in a local database of the electronic programmer 120, or in a remote database 200. In these embodiments, the patient records may be retrieved by the electronic programmer 120 and displayed in the user interface 250, and may be edited/updated using the interface 250. After the updating or editing is finished, the patient records may then be sent back to its place of original storage. In other embodiments, corresponding copies of the patient records may also be stored in more than one place, for example the copies may be stored in the medical devices 110, the local database of the electronic programmer 120, and the remote database 200. In these embodiments, the patient records may still be updated/edited through the user interface 250, and thereafter these patient records may be synched with their corresponding copies stored elsewhere. In some embodiments, the synching of the patient records may require a correct password entry.

As is shown in FIGS. 3-4, the display of visual identification information in the patient records facilitates the association between a patient and his or her respective medical device. When a healthcare professional queries a list of nearby medical devices that are ready for programming, he can immediately recognize which medical device belongs to the target patient for whom the stimulation therapy is to be delivered. Previously, the healthcare professional may have to somehow manually match the patient's textual information with the serial number each medical device returned by a query, which can be time-consuming and boring, and also error-prone. As a result, programming may be delivered to the wrong medical device or wrong patient. Now, the patient's visual information appears along with the linked medical device information. The healthcare professional can therefore quickly determine who the target patient is, and what medical device needs to receive programming accordingly. In this manner, the present disclosure reduces potential mistakes made in the medical device programming process.

Figures 5, 6:
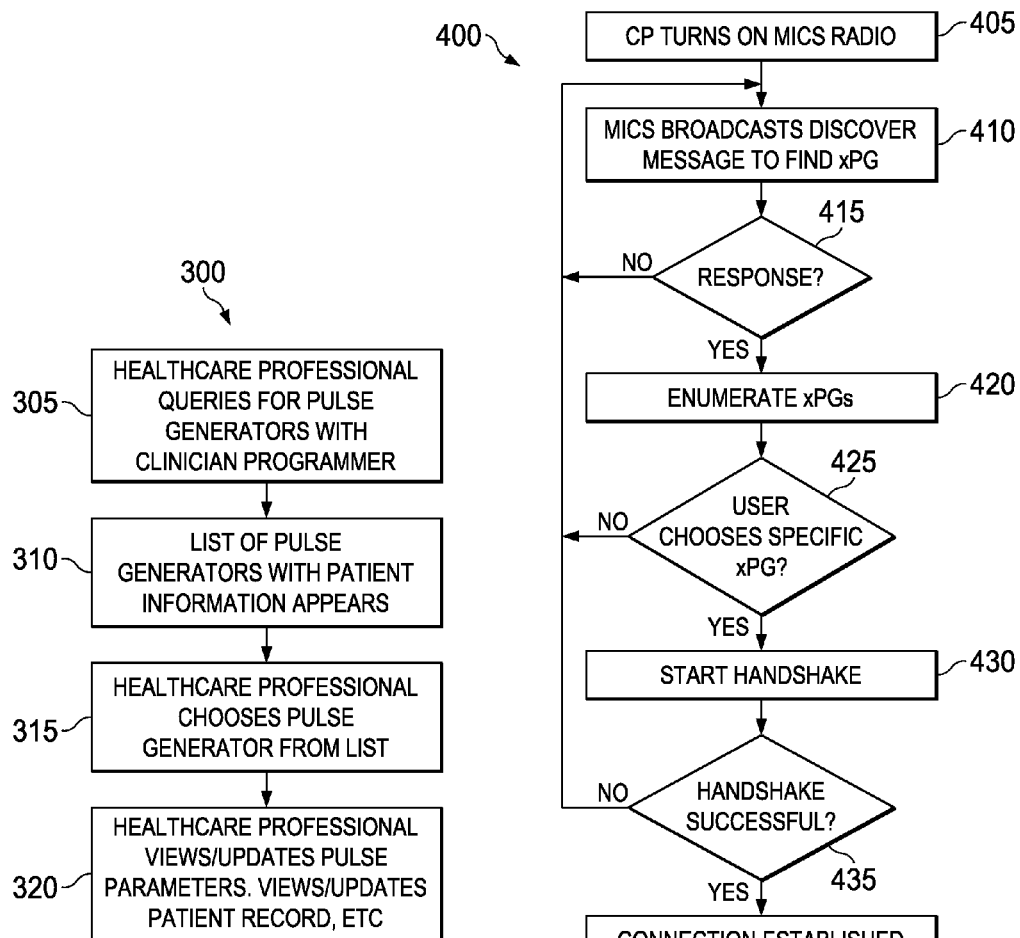
FIG. 5 is a flowchart of using an electronic programmer to find and communicate with nearby medical devices according to various aspects of the present disclosure.
FIG. 6 is a flowchart of a method of performing communication between an electronic programmer and a medical device according to various aspects of the present disclosure.

FIG. 5 is a flowchart of a simplified example method 300 that illustrates some of the various aspects of the present disclosure discussed above. Referring to FIG. 5, the method 300 includes step 305, in which the healthcare professional queries for pulse generators with a clinician programmer. The pulse generators are examples of the medical devices 110 discussed above, and the clinician programmer is an example of the electronic programmer 120 discussed above. The querying in step 305 may be done through wireless communications conducted through the MICS protocol.

The method 300 proceeds with step 310, in which the list of pulse generators with patient information appears on the clinician programmer as a result of the querying done in step 305. The query results may be displayed via a touch-sensitive graphical user interface implemented on a touchscreen of the clinician programmer. The pulse generators are linked with their respective patient's information. In some embodiments, the pulse generators are identified by unique medical device identifiers, such as a product and model number and/or a serial number. The patient information may include personal information of the patient, for example the visual identification information of the patient, such as electronic images and/or videos.

The method 300 proceeds with step 315, in which the healthcare professional chooses the desired pulse generator from the list displayed in step 310. In some embodiments, the healthcare professional may make his selection using a gesture-based input via the touchscreen on the clinician programmer.

The method 300 proceeds with step 320, in which the healthcare professional may view, update the stimulation parameters of the stimulation program, or update the patient record via the touch-sensitive graphical user interface. Thereafter, the healthcare professional may activate the stimulation programs to deliver the intended stimulation therapy to the target patient. Of course, the method 300 is not limited to the steps 305-320 shown in FIG. 5 and may include additional steps that are not described herein for the sake of simplicity.

FIG. 6 is a flowchart of a simplified example method 400 that illustrates the process of communication between an electronic programmer and a medical device according to some embodiments of the present disclosure. As examples, the electronic programmer is a clinician programmer, and the medical device is a pulse generator (xPG), which may be implantable (IPG) or external (EPG).

The method 400 includes step 405, in which the clinician programmer turns on its MICS radio. In step 410, the MICS radio of the clinician programmer broadcasts a discovery message across a wireless network to search for nearby xPGs. A subsequent decision step 415 then determines whether xPGs are found. If the answer is no, the method 400 loops back to step 410 again to continue broadcasting the discovery message. If the answer is yes, the method 400 proceeds to step 420 to enumerate the discovered xPGs. In another subsequent decision step 425, a determination is made as to whether to user (e.g., healthcare professional) has chosen a specific xPG. If the answer is no, the method 400 loops back to step 410 again to continue broadcasting the discovery message. If the answer is yes, the method 400 proceeds to step 430 to start a handshake procedure with the selected xPG (i.e., a handshake between the clinician programmer and the xPG). If the handshake is determined to be unsuccessful in step 435, the method 400 once again loops back to step 410 again to continue broadcasting the discovery message. If the handshake is successful, the method 400 proceeds to step 440 to establish a connection between the clinician programmer and the xPG. The method 400 then proceeds to step 445 to complete applicable tasks, such as stimulation programming or reprogramming, or updating the patient's record. The subsequent decision step 450 then determines whether the connection is finished. If the answer is no, the method 400 loops back to step 445 to complete whatever applicable tasks are remaining at this point. If the answer is yes, the method 400 proceeds to step 455, in which the clinician programmer turns its MICS radio off. In step 460, the MICS radio closes connections with external devices. Of course, the method 400 is not limited to the steps 405-460 shown in FIG. 6 and may include additional steps that are not described herein for the sake of simplicity.

Figure 7A:
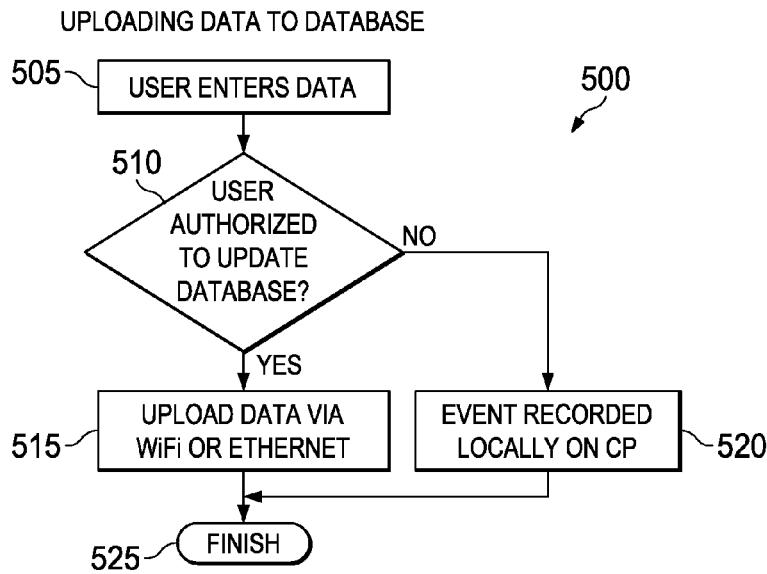
FIGS. 7A and 7B are flowcharts of methods of communications between an electronic programmer and a database according to various aspects of the present disclosure.
Figure 7B:
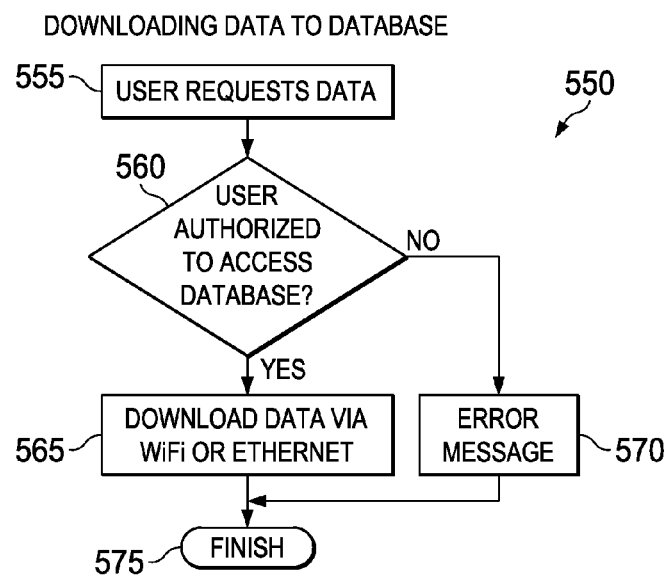

FIGS. 7A-7B are flowcharts of simplified example methods 500 and 550 that illustrate the process of communication between a healthcare professional (i.e., the user) using the clinician programmer (as an embodiment of the electronic programmer discussed above) and a remote database, for example the database 200 of FIG. 2. Referring first to FIG. 7A, the method 500 pertains to the uploading of data from the clinician programmer to the database. The method 500 includes step 505 in which the user enters data. Next, a decision step 510 determines whether the user is authorized to update the database. If the answer is yes, then the database is updated in step 515 by uploading data via a wireless or wired network, such as WiFi or Ethernet. If the user is not authorized to update the database, the method 500 proceeds to step 520, where the attempted update event is recorded locally on the clinician programmer. The method 500 thereafter finishes in step 525.

Referring first to FIG. 7B, the method 550 pertains to the downloading of data from the database to the clinician programmer. The method 500 includes step 555 in which the user requests data. Next, a decision step 560 determines whether the user is authorized to access the database. If the answer is yes, then the database is accessed in step 565 and the requested data is downloaded via a wireless or wired network, such as WiFi or Ethernet. If the user is not authorized to access the database, the method 550 proceeds to step 570, where an error message is displayed on the clinician programmer. The method 550 thereafter finishes in step 575.

Figure 8:
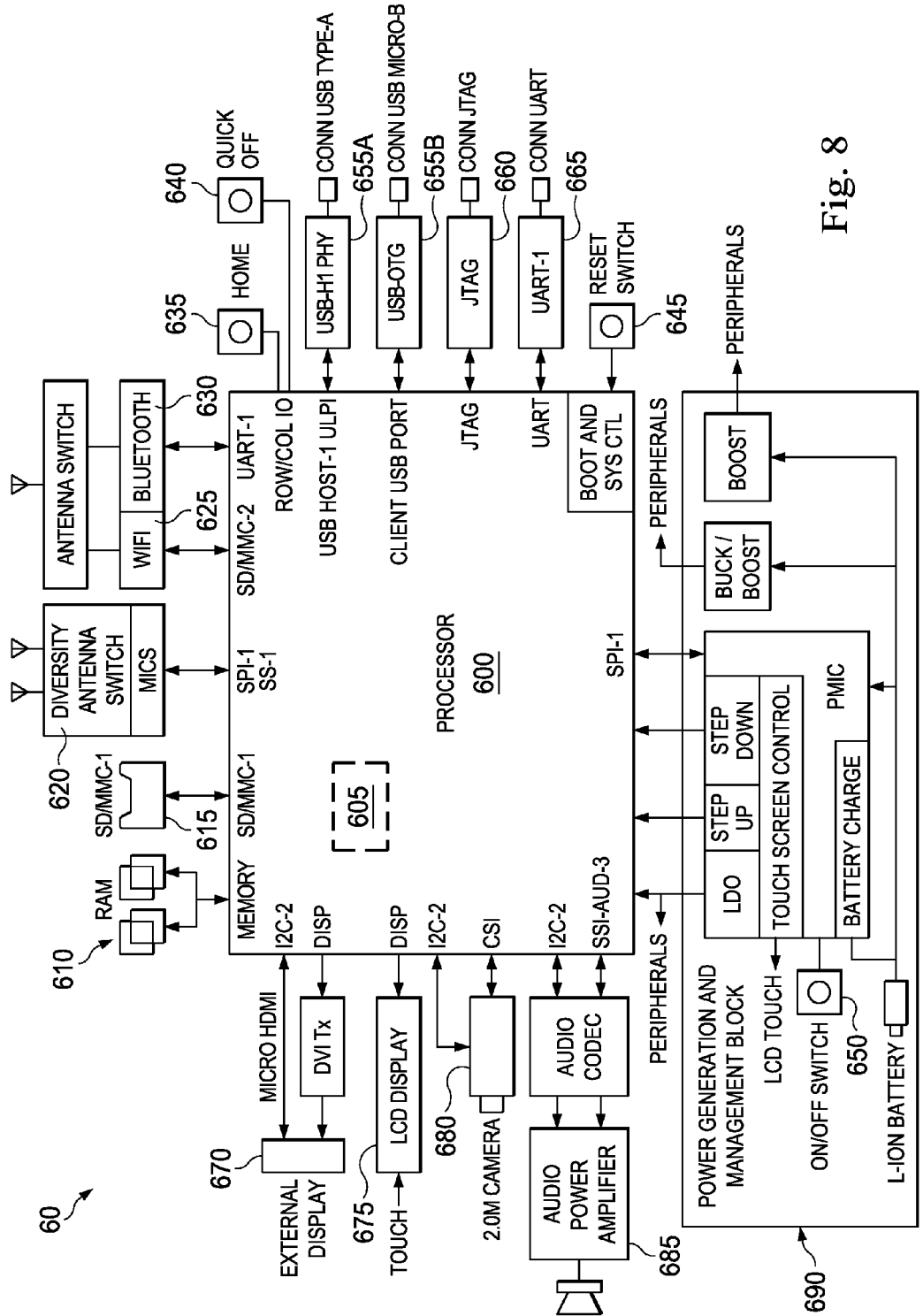
FIG. 8 is a simplified block diagram of an electronic programmer according to various aspects of the present disclosure.

FIG. 8 shows a block diagram of one embodiment of the clinician programmer (CP) 60 (FIG. 1) that can be used to display the visual representations of a medical therapy discussed above. It is understood, however, that alternative embodiments of the CP may be used to perform these representations as well.

The CP includes a printed circuit board ("PCB") that is populated with a plurality of electrical and electronic components that provide power, operational control, and protection to the CP. With reference to FIG. 8, the CP includes a processor 600. The processor 600 controls the CP. In one construction, the processor 600 is an applications processor model i.MX515 available from Freescale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Freescale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 8 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 8.

The CP includes multiple bi-directional radio communication capabilities. Specific wireless portions included with the CP are a Medical Implant Communication Service (MICS) bi-directional radio communication portion 620, a WiFi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The WiFi portion 625 and Bluetooth portion 630 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 8.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 8) may also be included for data transfer.

It is understood that a patient programmer may be implemented in a similar manner as the clinician programmer shown in FIG. 8.

Figure 9:
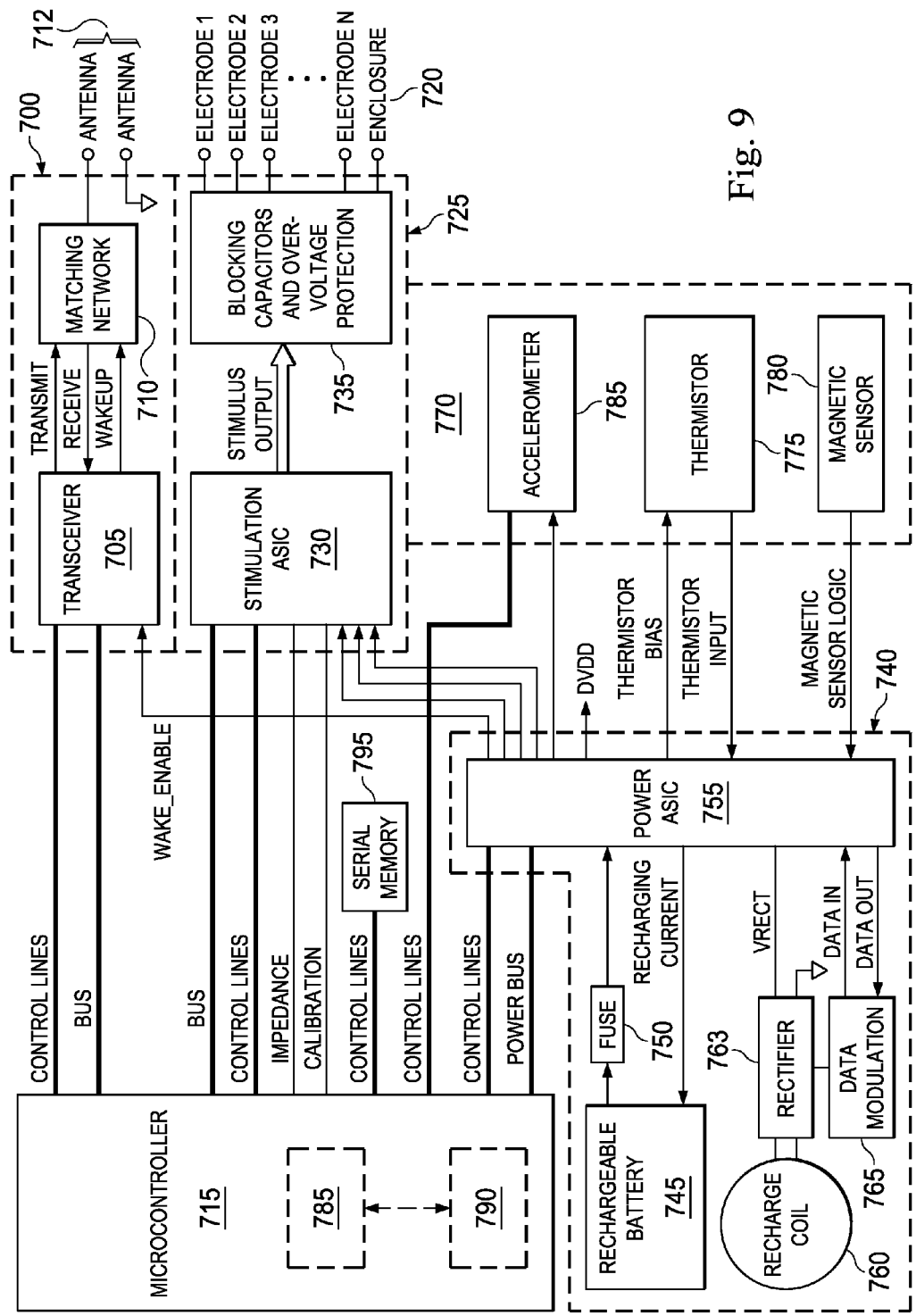
FIG. 9 is a simplified block diagram of an implantable pulse generator according to various aspects of the present disclosure.

FIG. 9 shows a block diagram of one construction of the implantable pulse generator (IPG) as an example of the medical device 110 discussed above. The IPG includes a printed circuit board ("PCB") that is populated with a plurality of electrical and electronic components that provide power, operational control, and protection to the IPG. With reference to FIG. 9, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG, as previously discussed, provides stimuli to electrodes of an implanted medical electrical lead (not illustrated herein). As shown in FIG. 9, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 9 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 10:
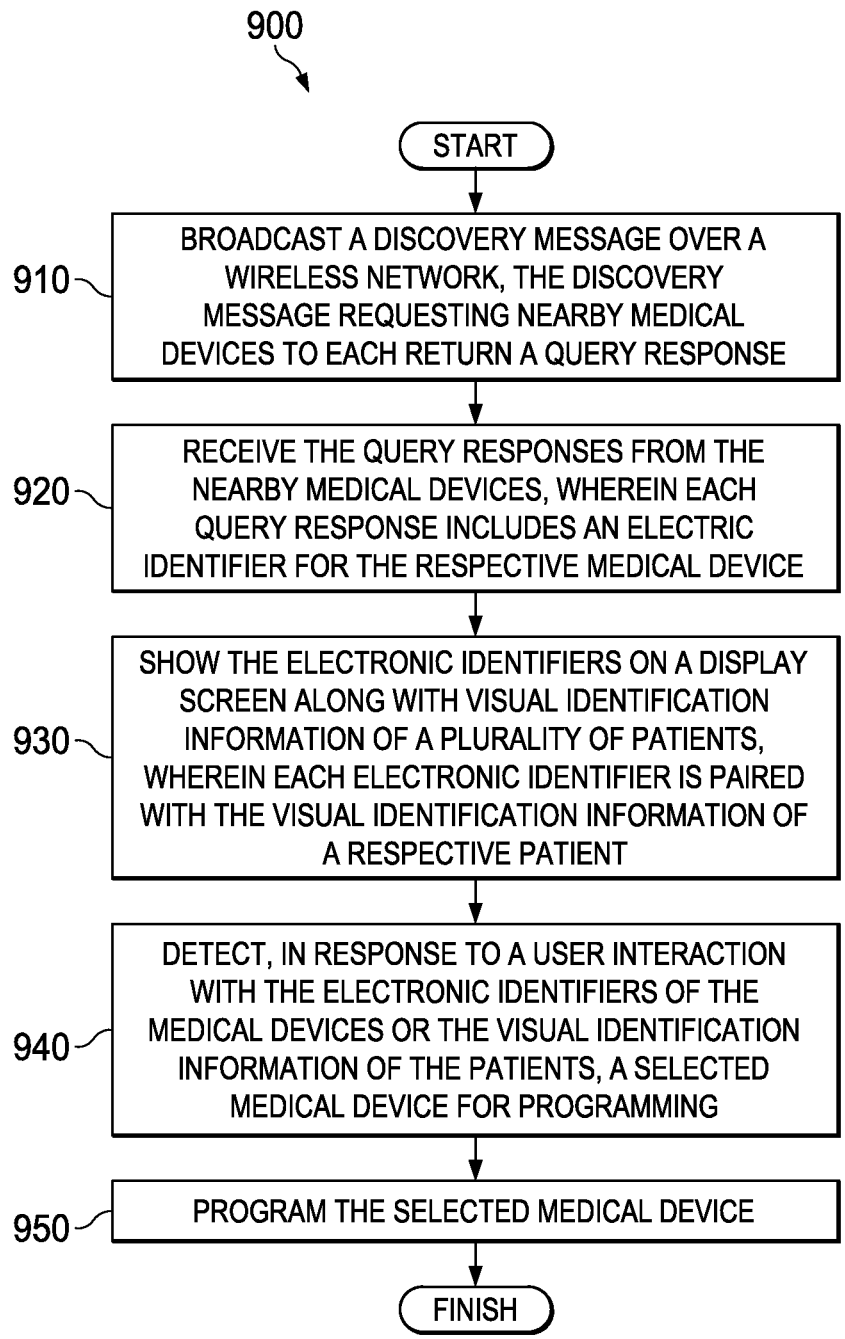
FIG. 10 is a method of associating patient information with medical devices according to various aspects of the present disclosure.

FIG. 10 is a flowchart of a method 900 of associating patient information with medical devices. As an example, the medical devices are pulse generators that are programmable by a clinician programmer to deliver a stimulation therapy to target patients. The method 900 includes example steps 910-950, which are each performed by the portable clinician programmer in the present embodiment. The communication between the medical device and the clinician programmer may be performed under a Medical Implant Communication Service (MICS) protocol.

In step 910, in which a discovery message is broadcast over a wireless network. The discovery message requesting nearby medical devices to each return a query response.

In step 920, in which the query responses are received from the nearby medical devices. Each query response includes an electronic identifier for the respective medical device. The visual identification information of patients may include at least one of: electronic photographs and electronic videos of the patient. In some embodiments, the visual identification information of each patient is stored in a specially partitioned memory storage of the medical device associated with the patient. The visual identification information is returned as a part of the query response for each medical device. In some embodiments, the electronic identifier for the medical device and the visual identification information of the patient are parts of an electronic patient record stored in the partitioned memory storage. The electronic patient record further includes at least some of the following information associated with the patient: name, residential address, email address, employment, phone number, birthdate, age, height, weight, blood type, medication taken, symptoms, and hospital identification number of the patient. In other embodiments, the visual identification information of all the patients may be stored in a memory storage of a portable clinician programmer, wherein the visual identification information of each patient is associated with a respective electronic identifier of the medical device.

In step 930, in which the electronic identifiers are shown on a display screen along with visual identification information of a plurality of patients. Each electronic identifier is paired with the visual identification information of a respective patient. In some embodiments, the display screen is a component of a clinician programmer and is a touch-sensitive screen. In some embodiments, the step 930 also includes sorting the electronic identifiers based on respective locations of their respective medical devices.

In step 940, in which a selected medical device is detected for programming in response to a user interaction with the electronic identifiers of the medical devices or the visual identification information of the patients.

In step 950, in which the selected medical device is programmed.

It is understood that the steps 910-950 of the method 900 described herein are merely example steps according to some embodiments. These steps may be omitted or modified in certain embodiments. In various other embodiments, the method 900 may also include additional steps performed before, during, or after the steps 910-950. As an example, the method 900 may include a step to update a remote electronic database based on the query responses received. As another example, the method 900 may include a step to update the electronic patient record in the medical device based on a corresponding copy thereof retrieved from the remote electronic database.

Figure 11B:
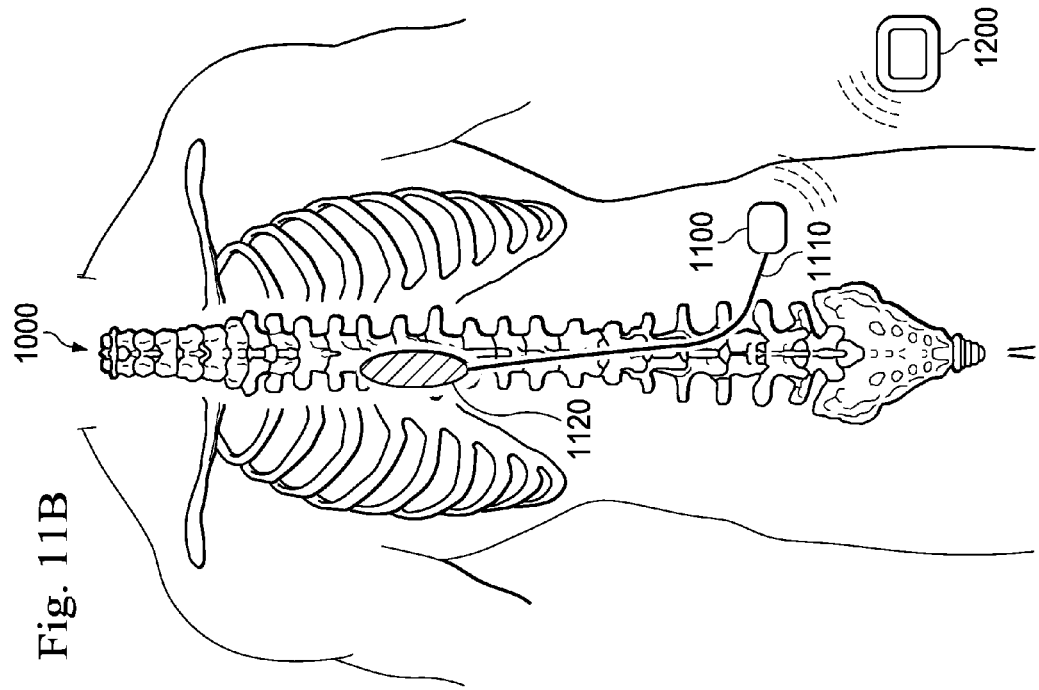
FIGS. 11A and 11B are side and posterior views of a human spine, respectively.
Figure 11A:
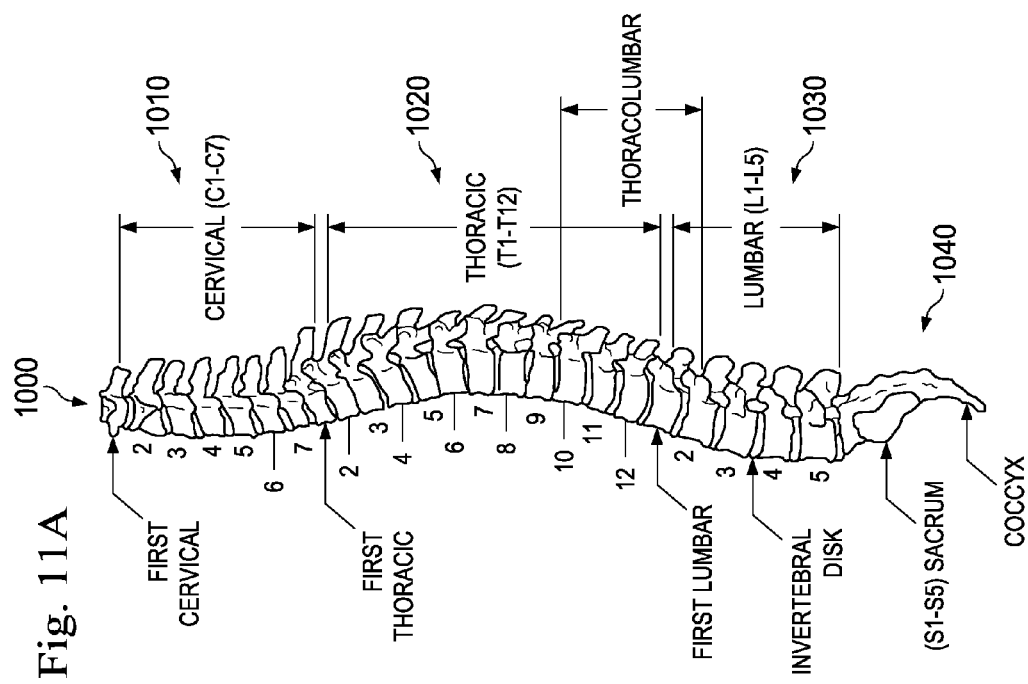

FIG. 11A is a side view of a spine 1000, and FIG. 11B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 11B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 8.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of associating patient information with medical devices, the method comprising:
   broadcasting a discovery message over a wireless network, the discovery message requesting a plurality of nearby medical devices to each return a query response;
   receiving the plurality of query responses from the plurality of nearby medical devices, wherein each query response includes a patient record stored in the respective medical device, and wherein the patient record include an electronic identifier for the respective medical device and visual identification information of a respective patient associated with the medical device;
   concurrently displaying portions of the plurality of patient records on a display screen, wherein each portion of the displayed patient record includes the electronic identifier of the respective medical device and the visual identification information of the respective patient associated with the medical device; and
   detecting, in response to a user interaction with the electronic identifiers of the medical devices or the visual identification information of the patients, a selected medical device for programming.

2. The method of claim 1, wherein the visual identification information of each patient is stored in a partitioned read-only memory storage of the medical device associated with the patient.

3. The method of claim 2, wherein the electronic patient record further includes at least some of the following information associated with the patient: name, residential address, email address, employment, phone number, birthdate, age, height, weight, blood type, medication taken, symptoms, and hospital identification number.

4. The method of claim 3, further comprising: updating the electronic patient record in the medical device based on a corresponding copy thereof retrieved from a remote electronic database.

5. The method of claim 2, further comprising: updating a remote electronic database based on the query responses received.

6. The method of claim 1, wherein digital copies of the visual identification information of all the patients are stored in a memory storage of a portable clinician programmer, and wherein the visual identification information of each patient is associated with a respective electronic identifier of the medical device.

7. The method of claim 6, further comprising: before the concurrently displaying, retrieving the visual identification information of the patients from the memory storage of the portable clinician programmer based on the electronic identifiers received from the query responses.

8. The method of claim 6, wherein the broadcasting, the receiving, and the detecting are each performed by the portable clinician programmer, and wherein the display screen is a component of the clinician programmer and is a touch-sensitive screen.

9. The method of claim 6, wherein the medical devices include pulse generators programmable by the clinician programmer to deliver a stimulation therapy to target patients.

10. The method of claim 1, further comprising:
    detecting a selection of one of the portions of the concurrently-displayed patient records; and
    thereafter displaying the selected patient record in its entirety.

11. The method of claim 1, further comprising: programming the selected medical device.

12. The method of claim 1, wherein the visual identification information of patients include at least one of: electronic photographs and electronic videos.

13. The method of claim 1, wherein the showing comprises: sorting the electronic identifiers based on respective locations of their respective medical devices.

14. The method of claim 1, wherein the broadcasting and the receiving are each performed at least in part under a Medical Implant Communication Service (MICS) protocol.

15. A portable electronic programmer for programming one or more medical devices to deliver a medical therapy to a patient, the portable electronic programmer comprising:
    a communications module configured to conduct electronic communication with external devices;
    a touch screen module configured to receive an input from a user and display an output to the user;
    a memory storage module configured to store machine-readable instructions; and
    a computer processor module configured to execute machine-readable instructions to perform the following tasks:
        discovering, at least in part via the communications module, a plurality of nearby medical devices;
        extracting a plurality of patient records from at least a subset of the nearby medical devices, wherein each patient record is stored electronically in a respective one of the nearby medical devices in the subset, and wherein each patient record contains visual identification information for a respective patient and a unique identifier for the medical device on which the patient record is stored; and
        displaying an arrangement of the plurality of patient records on the touch screen module, including concurrently displaying excerpts of the plurality of patient records, wherein each displayed excerpt of the patient record contains the visual identification information for the respective patient and the unique identifier for the respective medical device associated with the respective patient.

16. The portable electronic programmer of claim 15, wherein the computer processor module is configured to execute the machine-readable instructions to further perform:
    detecting, via the touch screen module, a user selection of a displayed excerpt of a target patient record in the arrangement of the patient records;
    displaying, in response to the detecting, a more detailed version of the target patient record; and
    programming the medical device identified by the target patient record.

17. The portable electronic programmer of claim 15, wherein the computer processor module is configured to execute the machine-readable instructions to further perform:
    accessing a remote database configured to electronically store a plurality of patient records for a plurality of patients, respectively, wherein at least some of the patient records stored in the remote database correspond with the patient records stored on the medical devices; and
    synching the patient records stored in the remote database with their corresponding patient records stored on the medical devices.

18. The portable electronic programmer of claim 15, wherein:
    the medical devices include neurostimulators; and
    the portable electronic programmer includes a clinician programmer configured to program stimulation parameters of the neurostimulator.

19. The portable electronic programmer of claim 15, wherein the communications module is configured to conduct electronic communication with the medical devices under a wireless communications protocol.

20. The portable electronic programmer of claim 15, wherein the arrangement of patient records includes a list that is sortable by a proximity of the portable electronic programmer to the medical device identified by each patient record.

21. The portable electronic programmer of claim 15, wherein the arrangement of patient records includes a list that is sortable alphabetically based on names of patients identified by the patient records.

22. The portable electronic programmer of claim 15, wherein the visual identification information for the patient contains at least one of: an electronic picture of the patient and an electronic video of the patient.

23. The portable electronic programmer of claim 15, wherein each patient record further includes one or more of the following patient data: name, birthdate, age, height, weight, blood type, and hospital identification number of the patient, and a treatment protocol for the patient.

24. A medical system, comprising:
    a medical device configured to deliver a medical therapy to a patient and store an electronic patient record, the electronic patient record containing a unique identifier of the medical device, personal information of the patient that includes visual identification information of the patient, and one or more treatment programs for programming the medical device to deliver the medical therapy to the patient; and
    a clinician programmer configured to program the medical device, wherein the clinician programmer includes:
        a display screen;
        a transceiver configured to establish electronic communications with a plurality of nearby medical devices that each store a respective electronic patient record, the medical device being one of the plurality of nearby medical devices;
a memory storage configured to store machine-readable code; and
a computer processor configured to execute the machine-readable code to:
display an arrangement of the plurality of electronic patient records on the display screen, including concurrently displaying excerpts of the plurality of electronic patient records, wherein each displayed excerpt of the electronic patient record contains the visual identification information of the patient associated with the electronic patient record and the unique identifier of the respective medical device associated with said patient.

25. The medical system of claim 24,
wherein the visual identification information and the unique identifier of the medical device are displayed side-by-side for each of the concurrently-displayed electronic patient records.

26. The medical system of claim 25, wherein the concurrently displaying comprises displaying excerpts of each of the plurality of the electronic patient records, and further comprising:
detecting a user selection of one of the excerpts of the plurality of electronic patient records; and
displaying, in response to the detecting, a more detailed version of the selected electronic patient record.

27. The medical system of claim 25, wherein the plurality of the electronic patient records is displayed as a list sortable by proximity to the clinician programmer or by an alphabetical order.

28. The medical system of claim 25, wherein the clinician programmer is configured to:
detect, via the display screen, a user selection of a target electronic patient record in the list; and
program the medical device on which the target electronic patient record is stored.

29. The medical system of claim 24, further comprising: a remote database configured to electronically store a plurality of electronic patient records for a plurality of patients, respectively, wherein the electronic patient record on the medical device has a corresponding electronic patient record in the remote database.

30. The medical system of claim 29, wherein the clinician programmer is configured to access the remote database to perform at least one of the following tasks:
update the electronic patient record on the medical device with its corresponding electronic patient record in the remote database; and
update the electronic patient record in the remote database with its corresponding electronic patient record on the medical device.

31. The medical system of claim 24, wherein the visual identification information of the patient includes at least one of: an electronic photograph of the patient and an electronic video of the patient.

32. The medical system of claim 24, wherein the first partition is configured to prevent the personal information of the patient from being replaced by personal information of the different patient by way of password-protected access.

33. The medical system of claim 24, wherein the display screen is a touch-sensitive screen.

34. The medical system of claim 24, wherein the medical device includes a pulse generator.

35. The medical system of claim 24, wherein the clinician programmer is configured to establish the electronic communication with the medical device via a wireless communications protocol.

36. A medical system, comprising:
one or more programmable pulse generators each configured to deliver a respective stimulation therapy to a respective patient, wherein the one or more programmable pulse generators each include:
a transceiver component configured to conduct telecommunications with an external electronic programmer to receive one or more stimulation programs;
a first memory storage divided partitioned into a plurality of partitions, wherein a first one of the partitions is configured to store the stimulation programs, and wherein a second one of the partitions is configured to store an electronic patient record containing personal information of the patient including visual identification information of the patient, wherein the first one of the memory partitions is configured to block data associated with the personal information of the patient from being written therein, and the second one of the memory partitions is configured to allow the personal information of the patient to be updated through password-protected access but prevent the personal information of the patient from being replaced by personal information of a different patient; and
microcontroller and stimulation circuitry configured to generate electrical pulses of the stimulation therapy based on the stimulation programs; and
the electronic programmer configured to program the one or more programmable pulse generators, wherein the electronic programmer includes:
a touch-sensitive graphical user interface configured to receive an input from a user and display an output to the user;
a communications component configured to conduct electronic communications with the one or more programmable pulse generators;
a second memory storage configured to store machine-readable code; and
a computer processor configured to execute the machine-readable code to display, via the touch-sensitive graphical user interface, an arrangement of the electronic patient records stored on the one or more programmable pulse generators, including concurrently displaying excerpts of the electronic patient records, wherein each displayed excerpt of the electronic patient record contains the visual identification information of the patient associated with the electronic patient record and a unique identifier of the respective programmable pulse generator associated with said patient.

37. The medical system of claim 36, wherein the computer processor is configured to execute the machine-readable code to further perform:
detecting, via the touch-sensitive graphical user interface, a user selection of a displayed excerpt of a target patient record in the arrangement of the electronic patient records;
displaying, via the touch-sensitive graphical user interface and in response to the detecting, a more detailed version of the target patient electronic record; and
sending programming instructions to the programmable pulse generator identified by the target electronic patient record.

38. The medical system of claim 36, wherein the second one of the memory partitions is configured to become read-only after the personal information of the patient is written therein.

39. The medical system of claim 36, wherein the visual identification information of the patient includes at least one of: an electronic photograph of the patient and an electronic video of the patient.

40. The medical system of claim 36, wherein the electronic programmer includes a clinician programmer.

41. The medical system of claim 36, wherein the second partition further contains at least some of the following personal information of the patient: name, residential address, email address, employment, phone number, birthdate, age, height, weight, blood type, medication taken, symptoms, and hospital identification number, and treatment programs of the patient.

42. The medical system of claim 36, wherein the telecommunications are conducted under a Medical Implant Communication Service (MICS) protocol.

\* \* \* \* \*